United States Patent
Fischer et al.

(10) Patent No.: US 11,384,039 B2
(45) Date of Patent: *Jul. 12, 2022

(54) PROCESS FOR THE SEPARATION OF DIOLS

(71) Applicant: SHELL OIL COMPANY, Houston, TX (US)

(72) Inventors: Kai Jürgen Fischer, Amsterdam (NL); Carmelo Perez Golf, Amsterdam (NL); Pieter Huizenga, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 902 days.

This patent is subject to a terminal disclaimer.

(21) Appl. No.: 16/303,196

(22) PCT Filed: May 19, 2017

(86) PCT No.: PCT/EP2017/062168
§ 371 (c)(1),
(2) Date: Nov. 20, 2018

(87) PCT Pub. No.: WO2017/202731
PCT Pub. Date: Nov. 30, 2017

(65) Prior Publication Data
US 2020/0325090 A1    Oct. 15, 2020

(30) Foreign Application Priority Data
May 23, 2016    (EP) .................................... 16170888

(51) Int. Cl.
*C07C 29/84* (2006.01)
*C07C 29/80* (2006.01)

(52) U.S. Cl.
CPC .............. *C07C 29/84* (2013.01); *C07C 29/80* (2013.01)

(58) Field of Classification Search
CPC ................................ C07C 29/84; C07C 29/80
See application file for complete search history.

(56) References Cited

U.S. PATENT DOCUMENTS

| | | | |
|---|---|---|---|
| 4,935,102 A | 6/1990 | Berg | |
| 4,966,658 A | 10/1990 | Berg | |
| 5,076,896 A | 12/1991 | Carduck et al. | |
| 5,423,955 A | 6/1995 | Berg | |
| 7,812,200 B2 | 10/2010 | Franke et al. | |
| 10,221,116 B2 | 3/2019 | Huizenga et al. | |
| 10,246,390 B2 | 4/2019 | Huizenga et al. | |
| 10,308,577 B2 * | 6/2019 | Perez Golf | ............. C07C 29/84 |
| 2011/0312050 A1 | 12/2011 | Zhang et al. | |
| 2012/0184783 A1 | 7/2012 | Bamicki | |
| 2013/0284584 A1 | 10/2013 | Xiao et al. | |
| 2016/0090342 A1 | 3/2016 | Fischer et al. | |

FOREIGN PATENT DOCUMENTS

| | | | |
|---|---|---|---|
| CN | 1634823 A | 7/2005 | |
| CN | 102372600 A | 3/2012 | |
| CN | 102643165 A | 8/2012 | |
| CN | 103467246 A | 12/2013 | |
| WO | 2008057317 A1 | 5/2008 | |
| WO | WO-2008057263 A2 * | 5/2008 | ............. C07C 45/81 |
| WO | 2009068110 A1 | 6/2009 | |
| WO | 2015150520 A1 | 10/2015 | |

OTHER PUBLICATIONS

Burke ("Solubility Parameters: Theory and Application", The American Institute of Conservation, The Book and Paper Group Annual, vol. Three, 1984, 18 pages) and Cockrem (WO 2008/057263 A2). (Year: 1984).*

Yufeng et al., "Study on Separation of Glycol and 1, 2-propanediol by Heterogeneous Azeotropic Distillation", Contemporary Chemical Industry, vol. 40, Issue No. 6, Jun. 30, 2011, pp. 560-561, 564 (English Abstract).

International Search Report and Written Opinion received for PCT Patent Application No. PCT/EP2015/078680, dated Jan. 25, 2016, 9 pages.

Rogalski et al., "Ebulliometers modified for the accurate determination of vapour-liquid equilibrium", Fluid Phase Equilibria, vol. 5, Issues 1-2, 1980, pp. 97-112.

Ronghui et al., "Research Progress on Purification Technology of Ethylene Glycol Crude Product From Nonpetroleum Route", Applied Chemical Industry, vol. 42, Issue No. 11, Nov. 2013, 6 pages (English Abstract).

International Search Report and Written Opinion received for PCT Patent Application No. PCT/EP2016/072465, dated Dec. 19, 2016, 8 pages.

International Search Report and Written Opinion received for PCT Patent Application No. PCT/EP2017/062153, dated Aug. 28, 2017, 8 pages.

International Search Report and Written Opinion received for PCT Patent Application No. PCT /EP2017/062168, dated Aug. 2, 2017, 9 pages.

* cited by examiner

*Primary Examiner* — Rosalynd A Keys
(74) *Attorney, Agent, or Firm* — Shell USA, Inc.

(57) ABSTRACT

The invention provides a process for the separation of a first C3 to C7 diol from a first mixture of C3 to C7 diols. The first mixture is provided to a first distillation column. An extractant is fed to the first distillation column above the first mixture. A stream comprising the first diol and the extractant is removed as a bottoms stream from the first distillation column and subjected to distillation in a second distillation column. A high purity first diol stream is removed from the top section of the second distillation column, while a used extractant stream is removed from the bottom section. The extractant is a C3 to C6 sugar alcohol or mixture thereof. The first diol is a close-boiler to and/or forms an azeotrope with one or more of the other C3 to C7 diols present in the first mixture.

12 Claims, 1 Drawing Sheet

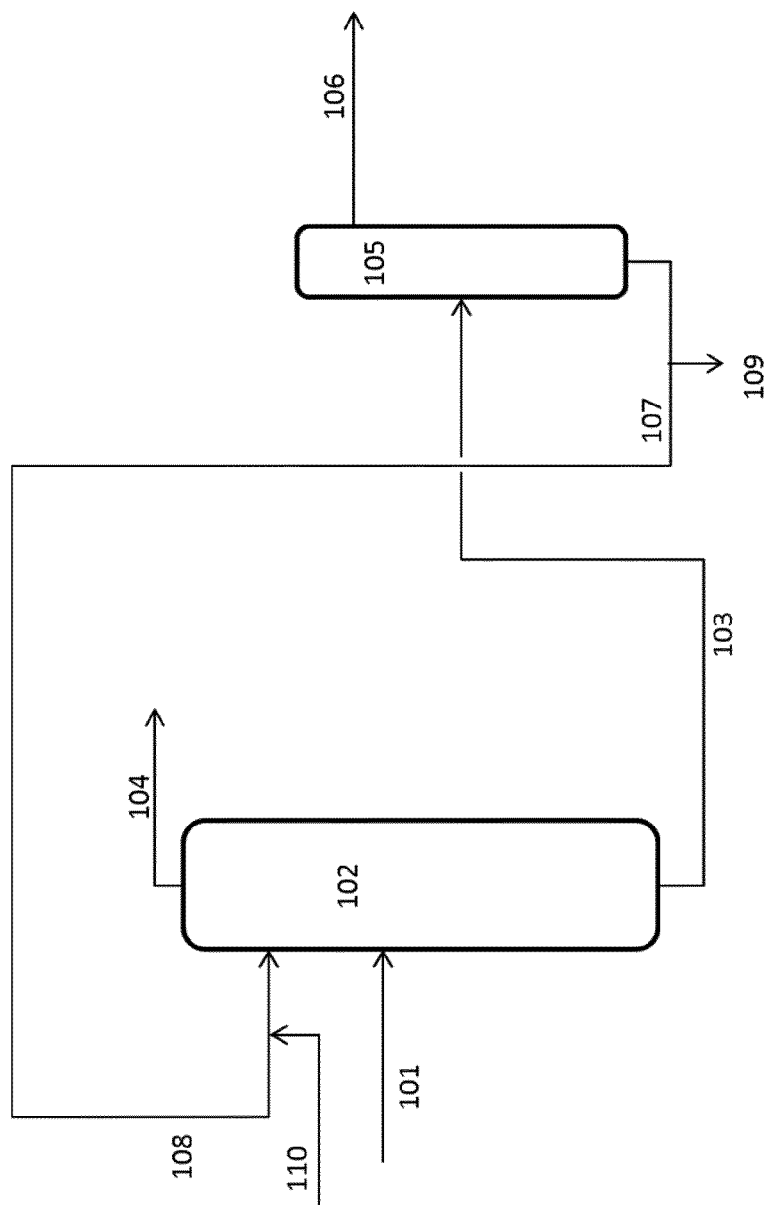

US 11,384,039 B2

PROCESS FOR THE SEPARATION OF DIOLS

CROSS REFERENCE TO RELATED APPLICATIONS

This is a national stage application of International Application No. PCT/EP2017/062168, filed 19 May 2017, which claims benefit of priority to European Patent Application No. 16170888.8, filed 23 May 2016.

FIELD OF THE INVENTION

The present invention relates to a process for the selective separation of diols.

BACKGROUND OF THE INVENTION

Diols, and especially glycols are valuable materials with a multitude of commercial applications, e.g. as heat transfer media, antifreeze, and precursors to polymers. Glycols are typically made on an industrial scale by hydrolysis of the corresponding alkylene oxides, which are the oxidation products of alkenes, produced from fossil sources.

In recent years, increased efforts have focused on producing chemicals, including glycols, from renewable feedstocks, such as sugar-based materials. For example, US20110312050 describes a continuous process for the catalytic generation of polyols from cellulose, in which the cellulose is contacted with hydrogen, water and a catalyst to generate an effluent stream comprising at least one polyol.

CN102643165 is directed to a catalytic process for reacting sugar in an aqueous solution with hydrogen in the presence of a catalyst in order to generate polyols, especially diols.

As with many chemical processes, the reaction product stream in these reactions comprises a number of desired materials, diluents, by-products and other undesirable materials. In order to provide a high value process, the desirable product or products must be obtainable from the reaction product stream in high purity with a high percentage recovery of each product and with as low as possible use of energy and complex equipment.

In known processes to make diols, and in particular glycols, the diols are usually present at high dilution in a solvent, typically water. The solvent is usually removed from the diols by distillation. Subsequent purification of the diols is then carried out by fractional distillation. This process can have high costs both in terms of capital and operational expenditure.

When diols are produced by hydrogenolysis of sugars, a mixture of diols is produced. The main diol constituents in the reaction product stream are monoethylene glycol (MEG), monopropylene glycol (MPG) and 1,2-butanediol (1,2-BDO). Other diols, such as 2,3-butanediol (2,3-BDO), pentanediols, hexanediols and heptanediols are also generally present. The separations of a number of these diols by distillation is challenging due to the similarity in their boiling points. Purification may be complicated as certain diols form homogeneous minimum boiling azeotrope with each other at vacuum and at atmospheric pressures. An example of a close-boiling, azeotrope-forming glycol pair is MPG and 2,3-pentanediol. Other azeotropic mixture may be formed between other diols present further complicating the purification process.

Degradation of the products at high temperatures prevents higher than atmospheric pressure being used for distillation. U.S. Pat. No. 4,966,658 is directed to the separation of a mixture of 1,2-BDO and MEG using a process known as azeotropic distillation in which an azeotrope-forming agent is added to the mixture before distillation in order to facilitate separation. A similar process is described in U.S. Pat. No. 5,423,955 for the separation of 1,2-BDO and MPG. Azeotropic distillation can lead to an increase in relative volatility between the components but also leads to further process steps in order to remove the azeotrope forming agents.

WO2015150520 discloses a process for separating monoethylene glycol from a mixture comprising monoethylene glycol and 1,2-butanediol, using a two column, pressure-swing distillation set-up.

It would be advantageous to provide a simple and efficient method to separate combinations of C3 to C7 diols often formed in processes for the production of diols. While many of these diols may often be seen as by-products, an efficient method for their separation and purification would add value to any process in which they are made.

SUMMARY OF THE INVENTION

Accordingly, the present invention provides a process for the separation of a first diol, selected from the group consisting of C3 to C7 diols from a first mixture comprising two or more C3 to C7 diols, said process comprising the steps of:
(i) providing said first mixture comprising two or more C3 to C7 diols as a feed to a first distillation column;
(ii) providing a feed comprising an extractant to the first distillation column above the first mixture;
(iii) operating the first distillation column at a temperature in the range of from 50 to 250° C. and a pressure in the range of from 0.1 to 400 kPa;
(iv) removing a stream comprising the first diol and the extractant as a bottoms stream from the first distillation column; and
(v) subjecting the stream comprising the first diol and the extractant to distillation in a second distillation column to provide a stream from the top-section of the second distillation column comprising the first diol in high purity and a stream from the bottom section of the second distillation column comprising a used extractant stream,
wherein the extractant is selected from the group of C3 to C6 sugar alcohols and mixtures thereof, and wherein the first diol is a close-boiler to and/or forms an azeotrope with one or more of the other C3 to C7 diols present in the first mixture.

BRIEF DESCRIPTION OF THE DRAWING

FIG. 1 is a schematic diagram of an exemplary, but non-limiting, embodiment of a process for the separation of diols as described herein.

DETAILED DESCRIPTION OF THE INVENTION

The present inventors have found that a first C3 to C7 diol can be effectively separated with high recovery and excellent product purity from a mixture comprising two or more C3 to C7 diols by distilling said mixture in a first distillation column wherein a feed of an extractant, comprising a C3 to C6 sugar alcohol or mixtures thereof, is provided at or near to the top of said first distillation column. The presence of the extractant in the first distillation column changes the relative volatilities of the diols and breaks any azeotropes that exist in the first diols mixture.

The first mixture comprises two or more C3 to C7 diols. Preferably, said two or more C3 to C7 diols, including said first diol, are selected from the group consisting of C3 to C7 glycols. The term glycol as used herein is given its usual meaning, i.e. a diol in which the two hydroxyl groups are present on vicinal carbon atoms. In a preferred embodiment, the first diol is monopropylene glycol (MPG) and the first mixture comprises, as glycols, at least MPG and 2,3-pentanediol.

The process may be applied to any mixture comprising two or more C3 to C7 diols. Preferably, the first mixture comprising two or more C3 to C7 diols is derived from the reaction product stream from a process for the production of diols. In a particularly preferred embodiment of the invention, the first mixture comprising two or more C3 to C7 diols is derived from the reaction product stream from a process for the hydrogenolysis of a saccharide-containing feedstock.

Typically, the reaction product stream from a process for the hydrogenolysis of a saccharide-containing feedstock comprises, as diols, at least MEG, MPG and 1,2-BDO. Other diols, such as 2,3-butanediol (2,3-BDO), pentanediols, hexanediols and heptanediols are also generally present. These diols are typically present at a concentration in the range of from 0.1 to 30 wt % of the overall stream. After removal of MEG from said process streams, it adds value to the processes to be able to separate and purify the remaining diols from the process stream As well as the diols, the reaction product streams from hydrogenolysis reactions of saccharides may comprise solvent (particularly water), oxygenates, hydrocarbons, catalyst, degradation products, and gases in any composition. The variety of compounds and their concentration depend on the saccharide-containing feedstock and the various hydrogenation and hydrogenolysis conversion conditions, including catalysts, reaction conditions such as temperature, pressure and saccharide concentration. However, suitably the hydrogenolysis reactions have gone to completion and the aqueous stream contains less than 5 wt %, preferably less than 2 wt %, more preferably less than 1 wt %, even more preferably less than 0.5 wt %, most preferably substantially no saccharides when considered as a weight percentage of the overall stream. Typically, the aqueous stream also contains less than 5 wt %, preferably less than 2 wt %, more preferably less than 1 wt %, even more preferably less than 0.5 wt %, most preferably substantially no glycerol, when considered as a weight percentage of the overall stream.

If the first mixture comprising two or more C3 to C7 diols is derived from such a reaction product stream, one or more treatment, separation and/or purification steps may be applied to the reaction product stream before the process of the present invention. Such steps may include one or more of: removal of at least a portion of the solvent present, for example by distillation; removal of light ends; fractional distillation to produce a diols stream and removal of heavy organics and any inorganics present, such as catalyst material; and initial separation steps to achieve preliminary separation of diols, e.g. process steps for the separation and purification of MEG.

The mixture comprising two or more C3 to C7 diols preferably has a weight ratio of the first diol:other C3 to C7 diols of at least 5:1. More preferably the weight ratio of the first diol:other C3 to C7 diols is at least 25:1.

The first mixture is provided as a feed to the first distillation column. Said first distillation column may be any suitable sort of column known in the art and may be equipped with trays or structured or unstructured packing. The number of theoretical trays may vary in the range of from 3 to 140 and may easily be determined by the skilled person on the basis of simple economic optimization experiments.

A feed comprising the extractant is provided to the first distillation column above point at which the first mixture feed is provided. Preferably, the feed comprising the extractant is provided at the top of or a few trays below the top of the first distillation column. As well as the extractant, this stream may also comprise sugar alcohol-like heavies, such as other polyhydric alcohols, from a recycle stream in the process.

The extractant is selected from the group of C3 to C6 sugar alcohols and mixtures thereof. Sugar alcohols have the general formula $HOCH_2(CHOH)_nCH_2OH$. Suitable sugar alcohols include glycerol, erythritol, threitol, arabitol, xylitol, ribitol, mannitol, sorbitol, galacticol and iditol. Although some of these sugar alcohols may be solid at room temperature and pressure, they can be used as liquids at suitable temperatures, pressures and compositions for suitable extractant mixtures in the process of the invention. In a preferred embodiment of the present invention, the extractant comprises glycerol.

Preferably, the extractant is added in an amount such that the weight ratio of the feed comprising the extractant to the first mixture comprising two or more C3 to C7 diols is at least 1:20, more preferably at least 1:10, even more preferably at least 1:4, based on the overall weight of the feed/mixture. Preferably, the ratio of the feed comprising the extractant to the first mixture comprising two or more C3 to C7 diols is at most 10:1, more preferably at most 5:1, even more preferably 2:1, more preferably at most 1.5:1, based on the overall weight of the feed/mixture.

The distillation in the first distillation column is carried out at a temperature in the range of from 50 to 250° C., preferably of from 100 to 200° C. and at a pressure of at least 0.1 kPa, preferably at least 10 kPa, more preferably at least 50 kPa. The pressure is at most 400 kPa, preferably at most 200 kPa, more preferably at most 120 kPa. It will be clear to the skilled person to vary the temperature and pressure in relation to each other in order to achieve suitable conditions.

A secondary stream comprising the remaining one or more C3 to C7 diols is removed from the first distillation column above the point at which the feed comprising the extractant is provided to the first distillation column. Preferably, the secondary stream is removed from the first distillation column as a condensed overheads stream.

A stream comprising the first diol and the extractant is removed from the first distillation column as a bottoms stream. Suitably, the diols content of this stream, comprises at least 95 wt % of the first diol fed to the first distillation column, preferably at least 98 wt % of the first diol, more preferably at least 99 wt % of the first diol, even more preferably at least 99.5 wt % of the first diol, most preferably at least 99.9 wt % of the first diol.

This stream is then subjected to a further distillation step in a second distillation column in which the first diol is distilled off to provide a first diol stream and a used extractant stream. This distillation is carried out at low pressure to avoid excessively high temperatures.

At least a portion of the first diol content is recovered as a high purity first diol product in a stream from the top-section of the second distillation column.

Optionally, a finishing section may be added to the top of the second distillation column in order to remove any type of light impurities/light degradation products formed at the separation process. This section would be above the point at which the high purity first diol stream is obtained.

At least a portion of the used extractant stream may then be recycled to the first distillation column as at least a portion of the feed comprising the extractant. Any heavies left that had been present in the first mixture comprising two or more C3 to C7 diols will also be present in the extractant stream to be recycled. If the first mixture comprising two or more C3 to C7 diols is derived from the reaction product stream from a process for the hydrogenolysis of a saccharide-containing feedstock, such heavies are likely to be sugar alcohol like in their structure, boiling point and other physical properties and may be recycled with the rest of the extractant stream.

A portion of this used extractant stream may be removed as a bleed in order to prevent a build-up of heavies. In this embodiment, fresh extractant will need to be provided to the first distillation column to make up the required amount of extractant. This fresh extractant should be provided to the first distillation column at the same height or above the used extractant stream.

Optionally, at least a portion of the used extractant stream may be subjected to further processing steps to further increase its purity.

Optionally, the first diol stream may be subjected to further processing steps to further increase its purity, remove trace components or meet the specifications for certain specific applications.

DETAILED DESCRIPTION OF THE DRAWINGS

The present invention is further illustrated in the preferred, but non-limiting, embodiment of the invention illustrated in FIG. 1.

In this description, the separation of high purity MPG from a mixture comprising MPG and 2,3-pentanediol from a saccharide hydrogenolysis process is described. The same system could be used to separate other mixtures.

In FIG. 1, a first mixture comprising two or more C3 to C7 diols (at least MPG and 2,3-pentanediol) is provided as a feed 101 to a first distillation column 102. A feed 108 comprising an extractant is also provided to the top section of the first distillation column 102. The distillation in the first distillation column is operated under conditions such that a stream 103 comprising the first diol (MPG) and the extractant is removed from the first distillation column 102 as a bottoms stream. A secondary stream 104 comprising the remaining one or more C3 to C7 diols (at least 2,3-pentanediol) is also removed from the first distillation column 102 as an overheads stream. The stream 103 comprising the first diol (MPG) and the extractant is provided to a second distillation column 105, which is then operated to provide the first diol as an overheads stream 106. The remaining used extractant is removed as the bottoms stream 107 of the second distillation column 105 and can be recycled to provide the feed 108 comprising the extractant. A bleed stream 109 may be removed from the extractant recycle stream in order to prevent a build-up of heavies.

Fresh extractant 110 may be added to the process as required.

EXAMPLES

The invention will be further illustrated by the following, non-limiting examples.

Aspen Plus software was used to model the process as shown in FIG. 1. A thermodynamic package was used. Said package resulted from fitting of experimental basic data of the vapour pressure curves for the individual components and the vapour-liquid equilibrium (VLE) measured for mixtures of those components. Examples were then generated using glycerol as the extractant (entrainer) and feed mixtures with different MPG/"Other diols" weight ratios and Glycerol/"MPG mixture" weight ratios to exemplify the separation and purification of a diol with 3 carbon atoms, in this case MPG. For this application, the separation of MPG from close boilers as 23-PDO species is a challenge since those glycols potentially form close-boiling point azeotropes when compared to the pure components.

The MPG mixture 101 is fed to the first (extractive) distillation column 102 at about the middle of its height. The glycerol feed 108 location is at the upper part of the first distillation column (first stages). The results for the first (extractive) distillation column 102 are shown in Table 1, below.

The results for the solvent recovery column 105 that provides final MPG 99.9% wt. purity with 99.9% recovery are shown in Table 2. This MPG last purification step comprises the distillation of MPG from the solvent in a second distillation (rectification) column with low number of stages and low reflux ratio, making use of the high relative volatility of the glycol (MPG) compared to the extractive solvents used.

Example 1—Separation and Purification of MPG from a Mixture with Other Diols

Initial MPG concentration of 97.6% wt. Glycerol/MPG mixture weight ratio of 7.3 towards first (extractive) distillation column; 99% MPG recovery and 98% 23-PDO recovery. Final MPG product purity of 99.97% wt.

TABLE 1

Results for the first (extractive) distillation column 102

|  | Feed MPG mixture | Feed Glycerol | Top | Bottom |
| --- | --- | --- | --- | --- |
| Temperature | 130.0° C. | 170.0° C. | 107.5° C. | 174.5° C. |
| Pressure | 1.2 Bar | 1.2 Bar | 0.05 Bar | 0.12 bar |
| Component | Wt. % | Wt. % | Wt. % | Wt. % |
| Glycerol | 0 | ≈100 | 1.6 | 88.3 |
| Sorbitol | 0 | 0 | 0.0 | 0.0 |
| Isosorbitol | 0 | 0 | 0.0 | 0.0 |
| MEG | 0 | 0 | 0.0 | 0.0 |
| MPG | 97.6 | ≈0 | 28.3 | 11.7 |
| 1,2-BDO | 0 | 0 | 0.0 | 0.0 |
| 2,3-BDO | 1.2 | 0 | 35.4 | 0.0 |
| 1,2-PDO | 0 | 0 | 0.0 | 0.0 |
| 2,3-PDO | 1.2 | 0 | 34.7 | 0.0 |
| 1,2-HDO | 0 | 0 | 0.0 | 0.0 |
| 1,2-HHDO | 0 | 0 | 0.0 | 0.0 |

PDO, HDO and HHDO make reference to pentanediol, hexanediol and heptanediols glycols, respectively.

TABLE 2

Results for the second distillation (solvent recovery) column 105

|  | Feed MPG mixture | Top MPG product | Bottom solvent |
| --- | --- | --- | --- |
| Temperature | 170° C. | 110.2° C. | 202.4° C. |
| Pressure | 1.2 Bar | 0.05 Bar | 0.06 bar |
| Component | Wt. % | Wt. % | Wt. % |
| Glycerol | 88.3 | ≈0 | 99.99 |
| Sorbitol | 0.00 | 0.00 | 0.00 |
| Isosorbitol | 0.00 | 0.00 | 0.00 |

TABLE 2-continued

Results for the second distillation (solvent recovery) column 105

|        | Feed MPG mixture | Top MPG product | Bottom solvent |
|--------|------------------|-----------------|----------------|
| MEG    | 0.00             | 0.00            | 0.00           |
| MPG    | 11.7             | 99.97           | 0.01           |
| 1,2-BDO| 0.00             | 0.00            | 0.00           |
| 2,3-BDO| 0.00             | 0.00            | 0.00           |
| 1,2-PDO| 0.00             | 0.00            | 0.00           |
| 2,3-PDO| 0.00             | 0.03            | 0.00           |
| 1,2-HDO| 0.00             | 0.00            | 0.00           |
| 1,2-HHDO| 0.00            | 0.00            | 0.00           |

That which is claimed is:

1. A process for the separation of a first diol, selected from the group consisting of C3 to C7 diols from a first mixture comprising two or more C3 to C7 diols, said process comprising the steps of:
   (i) providing said first mixture comprising two or more C3 to C7 diols as a feed to a first distillation column;
   (ii) providing a feed comprising an extractant to the first distillation column above the first mixture;
   (iii) operating the first distillation column at a temperature in the range of from 50 to 250° C. and a pressure in the range of from 0.1 to 400 kPa;
   (iv) removing a stream comprising the first diol and the extractant as a bottoms stream from the first distillation column; and
   (v) subjecting the stream comprising the first diol and the extractant to distillation in a second distillation column to provide a stream from the top-section of the second distillation column comprising the first diol in high purity and a stream from the bottom section of the second distillation column comprising a used extractant stream,
   wherein the extractant is selected from the group of C3 to C6 sugar alcohols and mixtures thereof, and wherein the first diol is a close-boiler to and/or forms an azeotrope with one or more of the other C3 to C7 diols present in the first mixture.

2. The process according to claim 1, wherein the extractant comprises glycerol.

3. The process according to claim 1, wherein the first diol is monopropylene glycol and the mixture comprising two or more C3 to C7 diols comprises at least monopropylene glycol and 2,3-pentanediol.

4. The process according to claim 1, wherein at least a portion of the used extractant stream is then recycled to the first distillation column as at least a portion of the feed comprising the extractant.

5. The process according to claim 1, wherein the feed comprising the extractant is provided at the top of or a few trays below the top of the first distillation column.

6. The process according to claim 1, wherein a portion of the used extractant stream is removed as a bleed stream.

7. The process according to claim 6, wherein fresh extractant is provided to the first distillation column, at the same height or above the used extractant stream, to make up the required amount of extractant.

8. The process according to claim 1, wherein the first mixture comprising two or more C3 to C7 diols is derived from the reaction product stream from a process for the hydrogenolysis of a saccharide-containing feedstock.

9. The process according to claim 1, wherein the mixture comprising two or more C3 to C7 diols has a weight ratio of the first diol:the other C3 to C7 diols of at least 5:1.

10. The process according to claim 1, wherein the extractant is added in an amount such that the weight ratio of the feed comprising extractant to the first mixture comprising two or more C3 to C7 diols is at least 1:20 and at most 10:1 based on the overall weight of the feed/mixture.

11. The process according to claim 1, wherein diols content of the stream comprising the first diol and the extractant, comprises at least 99.9 wt % of the first diol contained in the initial feed.

12. The process according to claim 1, wherein a finishing section is added to the top of the second distillation column above the point at which the high purity first diol stream is obtained, in order to remove any type of light impurities/light degradation products formed in the separation process.

* * * * *